United States Patent
Pascal et al.

(10) Patent No.: US 9,615,730 B2
(45) Date of Patent: *Apr. 11, 2017

(54) IN-VIVO IMAGING DEVICE WITH BACKSCATTER BLOCKING

(71) Applicant: GIVEN IMAGING LTD., Yoqneam (IL)

(72) Inventors: Amit Pascal, Haifa (IL); Zvika Gilad, Haifa (IL); Haim Bezdin, Rishon le'Zion (IL)

(73) Assignee: GIVEN IMAGING LTD., Yogneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/071,248

(22) Filed: Mar. 16, 2016

(65) Prior Publication Data

US 2016/0192833 A1  Jul. 7, 2016

Related U.S. Application Data

(63) Continuation of application No. 11/645,787, filed on Dec. 27, 2006, now Pat. No. 9,320,417, which is a continuation-in-part of application No. 11/319,769, filed on Dec. 29, 2005, now abandoned.

(51) Int. Cl.
*A61B 1/06* (2006.01)
*A61B 1/04* (2006.01)
*A61B 1/05* (2006.01)

(52) U.S. Cl.
CPC ............ *A61B 1/0661* (2013.01); *A61B 1/041* (2013.01); *A61B 1/051* (2013.01); *A61B 1/0607* (2013.01); *A61B 1/0676* (2013.01)

(58) Field of Classification Search
CPC ....... A61B 1/041; A61B 1/051; A61B 1/0607; A61B 1/0661; A61B 1/0676
See application file for complete search history.

(56) References Cited

U.S. PATENT DOCUMENTS

| | | | | |
|---|---|---|---|---|
| 7,347,817 B2* | 3/2008 | Glukhovsky | ...... | A61B 1/00186 600/160 |
| 8,262,566 B2* | 9/2012 | Gilad | ................. | A61B 1/00167 348/340 |
| 9,320,417 B2* | 4/2016 | Pascal | .................... | A61B 1/051 |

* cited by examiner

*Primary Examiner* — Ruth S Smith
(74) *Attorney, Agent, or Firm* — Pearl Cohen Zedek Latzer Baratz LLP (57) ABSTRACT

The invention provides a device for in-vivo imaging, for example, using an in-vivo imaging device including an imager a lens and an illumination source, all positioned behind a single viewing window. The in-vivo imaging device may include an element to block light from reaching a point of reflection on the inner surface of the viewing window, thereby preventing the light from being received by the imager.

17 Claims, 8 Drawing Sheets

IN-VIVO IMAGING DEVICE WITH BACKSCATTER BLOCKING

CROSS REFERENCE TO RELATED APPLICATIONS

This application is a continuation of U.S. patent application Ser. No. 11/645,787, filed on Dec. 27, 2006, entitled "IN-VIVO IMAGING DEVICE WITH BACKSCATTER BLOCKING", now U.S. Pat. No. 9,320,417, issued on Apr. 26, 2016, which is a continuation in part of U.S. patent application Ser. No. 11/319,769, filed on Dec. 29, 2005, entitled "IN-VIVO IMAGING OPTICAL DEVICE AND METHOD", which is now abandoned, all of which are incorporated herein by reference in their entirety.

FIELD OF THE INVENTION

The present invention relates to an in-vivo device for imaging; more specifically, the invention relates to a device for dealing with backscatter or stray light in an in-vivo imaging device.

BACKGROUND OF THE INVENTION

Autonomous in-vivo imaging devices, such as swallowable or ingestible capsules or other devices may move through a body lumen, imaging as they move along. In-vivo imaging may require in-vivo illumination, for example, using one or more illumination sources positioned inside the in-vivo imaging device, behind a viewing window of the device.

In such imaging devices backscatter and/or stray light from surfaces inside the device may often present a problem and reduce the information in the image obtained.

In order to avoid backscatter, designers of in-vivo imaging devices place, illumination source(s) and optical systems and/or imagers in specific positions relative to the viewing window, calculated to reduce backscatter to a minimum.

There is a need for a device and method that may avoid the damaging effects of backscatter and/or stray light while not being limited to specific design and positioning of illumination sources in an in vivo imaging device.

SUMMARY OF THE INVENTION

Embodiments of the present invention include an in-vivo imaging device having one or more illumination sources, an optical system and an imager all positioned behind a window. According to some embodiments the device includes a structure, typically a physical barrier, designed to block light from the illumination source from reaching a specific known spot on the window. According to embodiments of the invention a known spot or area is the spot or area from which internal light reflected off the window will be directed to the light receiving means, such as the optical system or imager. According to some embodiments the optical system may include an iris and the known spot is the spot on the window from which internally reflected light will be directed to the iris. The known spot or area may be calculated for each device, taking into account the positioning of the illumination sources relative to other components of the optical system and/or relative to the viewing window.

There is thus provided, according to embodiments of the invention, a device and method for obtaining images that are essentially free of stray light or backscatter.

According to embodiments of the invention a barrier or backscatter blocker in the in vivo imaging device is positioned so as to prevent light from an illumination source internal to an in vivo imaging device from reaching a spot on the viewing window of the in vivo imaging device from which such light will be internally reflected to the imager of the in vivo imaging device.

A capsule viewing window may be dome-shaped, for example an optical dome or cover and may cover an end of the device, protecting optical elements such as illumination source(s), imager(s) and a lens holder, which may be behind the dome.

In some embodiments, a backscatter blocker may be formed and/or shaped such that it blocks stray light from the illumination sources from directly reaching and/or flooding the imager(s).

In accordance with some embodiments there is provided an in vivo imaging device comprising:
a viewing window behind which are positioned;
an illumination source;
an imager; and
a blocking element positioned to block light from the illumination source from reaching a pre-calculated point on an internal surface of the viewing window.

In accordance with some embodiments, the pre-calculated point is defined by a point of reflection on the internal surface.

In accordance with some embodiments, the point of reflection is defined on the internal surface by light from the illumination source reflected to the imager in the absence of the blocking element.

In accordance with some embodiments, the blocking element is located between the illumination source and the point of reflection.

In accordance with some embodiments, the in vivo imaging device has a longitudinal axis parallel to the blocking element.

In accordance with some embodiments, the longitudinal axis is perpendicular to the blocking element.

In accordance with some embodiments, the in vivo imaging device comprises a lens holder and the blocking element is located on the lens holder.

In accordance with some embodiments, the blocking element is in close proximity to the illumination sources.

In accordance with some embodiments, the blocking element and the lens holder form a single integral unit.

In accordance with some embodiments, the blocking element is distal the imager.

In accordance with some embodiments, the blocking element is proximal the imager.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

It will be appreciated that the terms "receiving unit" and "imaging unit" relate to any unit suitable for receiving, processing or further transmitting illumination rays remitted from a target or data derived from these rays. For example, an imager or camera, such as a Charge Coupled Device (CCD) camera or imager or a Complementary Metal Oxide Semiconductor (CMOS) imager or camera may be used; other suitable receiving or imaging units may be used. According to some embodiments the term "receiving unit" may include an optical element suitable for receiving, processing or further transmitting illumination rays remitted from a target. An optical element may include for example, a lens.

A system according to some embodiments of the invention may include an in-vivo sensing device transmitting information (e.g., images and/or other data) to a data receiver and/or recorder possibly close to or worn on a subject. A data receiver and/or recorder may of course take other suitable configurations. The data receiver and/or recorder may transfer the received information to a larger computing device, such as a workstation or personal computer, where the data may be further analyzed, stored, and/or displayed to a user. In other embodiments, each of the various components need not be required and or may be housed in alternate configurations; for example, an internal device may transmit or otherwise transfer (e.g., by wire) information directly to a viewing or processing system. In another example, the data receiver or workstation may transmit or otherwise transfer information to the in-vivo device. While in one embodiment the device may be an autonomous capsule, other configurations, such as an endoscope or trocar may be used.

It is noted that some embodiments of the present invention may be directed to an autonomous, typically ingestible in-vivo device. Other embodiments need not be ingestible. Devices or systems according to embodiments of the present invention may be similar to embodiments described in US application publication number 2001/0035902 published on 1 Nov. 2001 and/or in U.S. Pat. No. 5,604,531, each of which are assigned to the common assignee of the present invention and each of which are hereby fully incorporated herein by reference. Furthermore, a receiving and/or display system suitable for use with embodiments of the present invention may also be similar to embodiments described in US publication number 2001/0035902 and/or in U.S. Pat. No. 5,604,531. Devices and systems as described herein may have other configurations and other sets of components.

Figure 1:
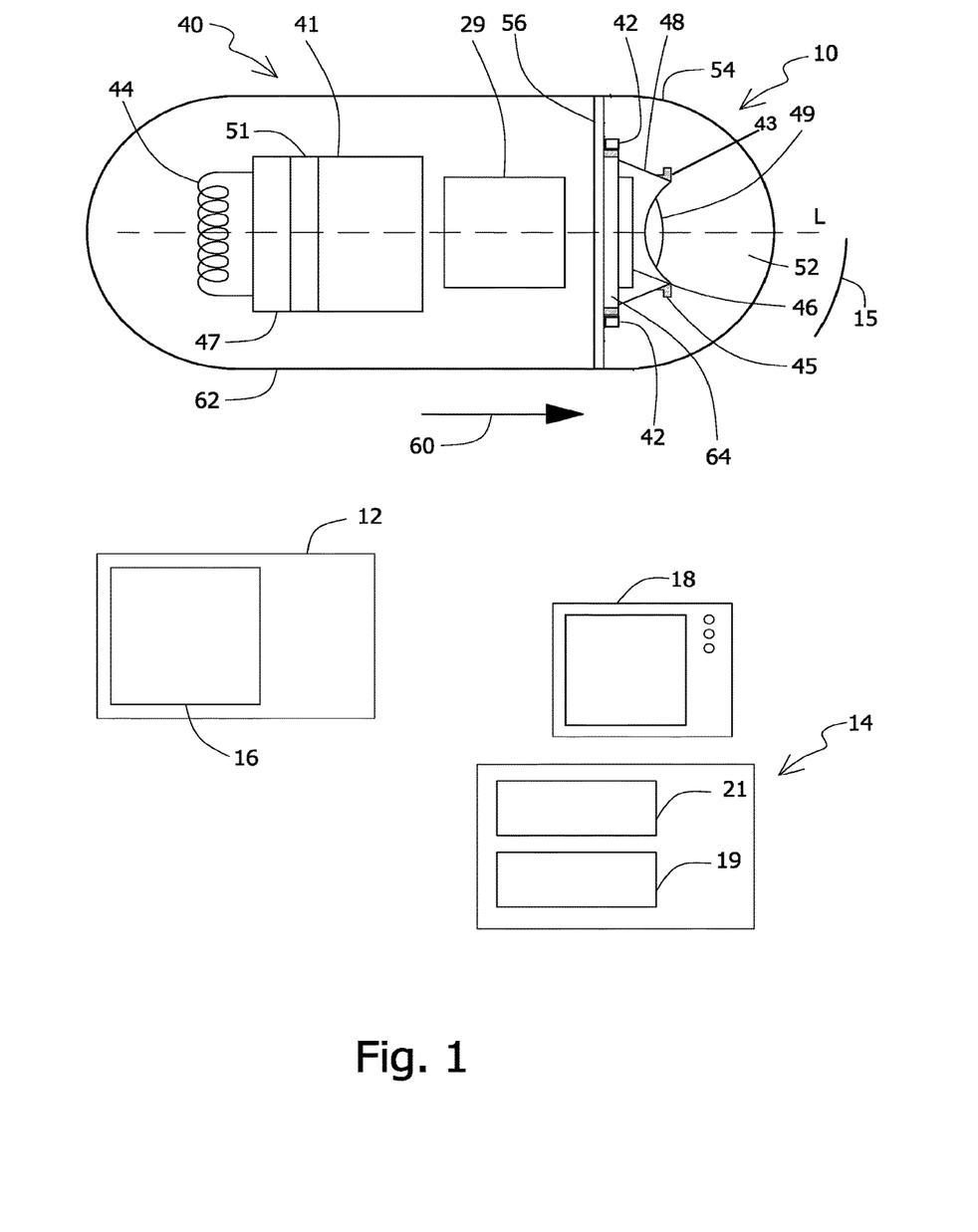
FIG. 1 is a schematic illustration of an in-vivo imaging system according to one embodiment of the present invention.

Reference is made to FIG. 1, which is a schematic diagram of a device and system according to one embodiment of the present invention. In one embodiment, the system may include an in-vivo imaging device, such as for example a device 40 which may, for example, be capsule shaped and have a longitudinal axis L, an optical system 10 including, for example, optical dome or viewing window 54, one or more lens(es) 49, lens holder or separator 48, an imager 46, one or more illumination source(s) 42 and backscatter blockers 43 and 45, also referred to herein as blocking elements, and one or more power source(s) 29. Power source(s) 29 may be, for example, a suitable battery, but in further embodiments may be other devices, such as a unit for receiving power from an external source. Viewing window 54, typically dome shaped, may typically define a space 52 behind which are positioned components such as imager 46, lens holder 48, one or more lenses 49, and one or more illumination source(s) 42. Window 54 may be a protective optical window, preferably made of plastic such as thermoplastic polyurethane resins, polymethyl, methacrylate, cyclic olefin copolymer, polycarbonates or other suitable plastic glass or ceramic transparent material. Typically, the imager 46 images via window 54 and illumination source(s) 42 illuminate via window 54. Lens holder 48 may be concentric with the longitudinal axis L and may include an aperture through which light reflected from, for example, an object 15 may be received. Device 40 may include a transmitter 41 (typically operating wirelessly via radio waves), and an antenna 44, for transmitting images and possibly other information to, for example, an external receiving device 12. Other types of transmitters and transmission methods may be used; for example, in an endoscope application, wire or other transmission may be used.

Device 40 may include a transceiver 51 that may be capable of receiving wireless signals and transmitting wireless signals; in some embodiments transceiver 51 may be a transmitter only and only transmission may occur. According to some embodiments transceiver 51 may be used instead of transmitter 41. Transceiver 51 may also have other functions. In some embodiments, transceiver 51 and a processor 47 may be included in a single integrated circuit. In some embodiments, antenna 44 may be used for both the receipt and transmission of wireless signals by transceiver 51. In other embodiments there may be more than one antenna. In some embodiments, device 40 may transmit but not receive signals.

According to some embodiments, imager 46 may be fixed or otherwise attached to a substrate such as, for example, a circuit board 64 or directly positioned onto a substrate 56. According to another embodiment of the invention, the various components of the device 40 may be disposed on a circuit board including rigid and flexible portions; preferably the components are arranged in a stacked vertical fashion. In other embodiments, circuit board 64 may be further attached to a substrate 56, which may for example support illumination source(s) 42 and which may define a viewing direction 60 of device 40.

Window 54 may form space 52, so that illumination source(s) 42, imager 46, and/or lens holder 48 may be recessed behind window 54. In one embodiment, an imaging device may include more than one image sensor. For example, an additional optical system may be included in a direction opposite viewing direction 60, to form for example a double ended viewing device. Other configurations for including more than one imager 46 in device 40 and/or more than one viewing direction may be implemented. Device 40, and other devices disclosed herein, may be used to view lumens such as the gastrointestinal tract in a natural state and/or in an unmodified form, not using or requiring techniques such as insufflation.

Typically, located outside the patient's body in one or more locations may be an image receiver 12, a data processor 14, and an image monitor 18. Image receiver 12 may include an image receiver storage unit 16. Data processor 14 may include a processor and/or CPU 19 and a storage unit 21.

The window 54 may be, for example part of a housing 62 of the device 40 and may preferably be made of plastic, glass, ceramic or other transparent material. Typically, the in vivo area to be viewed may be illuminated and viewed through the window 54, and thus components such as the imager 46 and illumination elements 42 may be behind the window 54, within the device 40.

Main body or housing 62 may be in some embodiments the tube of an endoscope or trocar, and thus may extend further rearward than may be depicted in the device 40 of FIG. 1. Imager 46 may include, for example, a CCD camera or imager, a CMOS camera or imager, a digital camera, a still camera, a video camera, or other suitable one or more imagers, cameras, receiving units or image acquisition components.

Device 40 may typically be or may typically include an autonomous swallowable capsule, which may be self contained, but device 40 may have other shapes and need not be swallowable or autonomous (e.g., device 40 may have other configurations, such as that of an endoscope or trocar). Device 40 may be in the form of a capsule or other unit where all the components may be substantially contained within a container, housing, or shell, and where device 40 may not require any wires or cables to, for example, receive power or transmit information and may be autonomous. In one embodiment, all of the components may be sealed within the device body (the body or shell may include more than one piece); for example, an imager, illumination units, power units, and transmitting and control units, may all be sealed within the device body. Device 40 may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

Transmitter 41 may include control capability, for example controlling the various operations of device 40, although control capability, or one or more aspects of control may be included in a separate component. In some embodiments of the present invention, transmitter 41 may typically be an ASIC (application specific integrated circuit), but may be of other constructions; for example, transmitter 41 may be a processor executing instructions. Device 40 may include a processing unit separate from transmitter 41 that may, for example, contain or process instructions.

Typically, located outside the patient's body in one or more locations may be an image receiver 12, a data processor 14, and an image monitor 18. Image receiver 12 may typically include an antenna or antenna array and an image receiver storage unit 16. Data processor 14 may include a processor 19 and a storage unit 21. Image monitor 18 may display, inter alia, images recorded by, for example, device 40. Typically, data processor 14 and monitor 18 may be part of a personal computer or workstation, which may include standard components such as a processor 19, a memory, a disk drive, and input-output devices, although alternate configurations are possible. Data processor 14 may typically, as part of its functionality, act as a controller controlling the display of the images. Image monitor 18 may typically be a conventional video display, but may, in addition, be any other device capable of providing images or other data and may be of any size monitor including large projection size monitors. The image monitor 18 may present the image data, typically in the form of still and/or a stream of image frames, and in addition may present other information. In an exemplary embodiment, the various categories of information may be displayed in windows. Other displaying formats may be used. In other embodiments of the present invention, one or more of the components included in receiver 12 and data processor and/or workstation 14 may be packaged in alternate configurations and may be or may be included in a portable or stationary device, package, and/or housing.

In operation, imager 46 may capture images and may send data representing the images to transmitter 41, which may transmit data to image receiver 12 using, for example, electromagnetic radio waves. Image receiver 12 may transfer the image data to image receiver storage unit 16. After a certain period of time of data collection, the image data stored in storage unit 16 may be transferred to the data processor 14 or the data processor storage unit 21. For example, the image receiver 12 or image receiver storage unit 16 may be taken off the patient's body and may be connected to a personal computer or workstation that may include the data processor 14 via a standard data link, e.g., a serial, parallel, USB, or wireless interface. According to one embodiment the image data may then be transferred from the image receiver storage unit 16 to data processor storage unit 21. Data processor 14, including possibly dedicated software, may analyze the data and provide the analyzed data to the image monitor 18, where a user views the image data. Other configurations allow for real time viewing. Further, other methods of recording, transmitting, storing and viewing images recorded by imager 46 may be used.

Figure 2A:
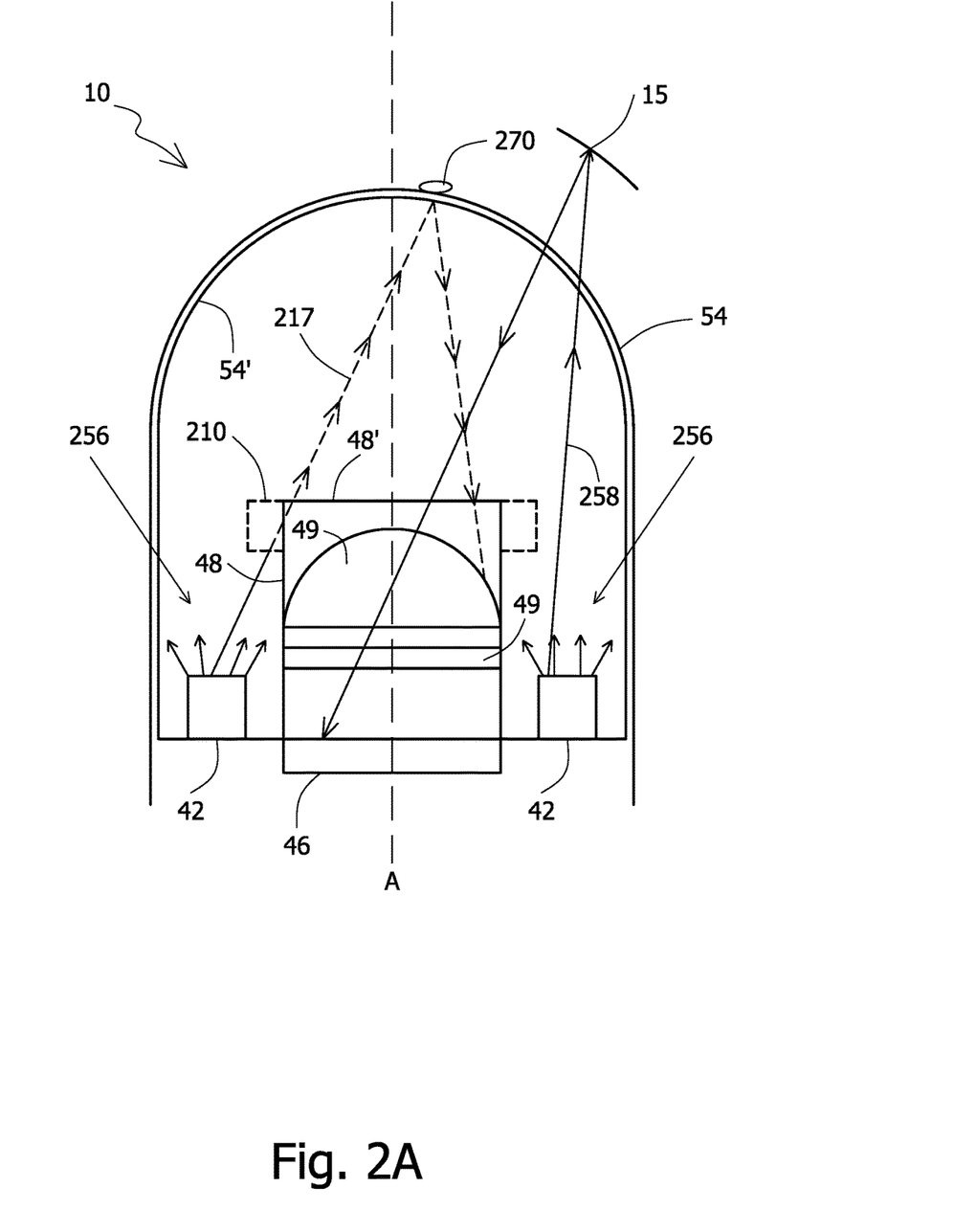
FIGS. 2A-2B are schematic presentations of an optical system according to an embodiment of the present invention.

Reference is now made to FIG. 2A, a schematic two dimensional presentation of an optical system according to an embodiment of the present invention. The optical system generally referenced as 10 may be included in, for example, device 40 of FIG. 1, but may be included in other suitable devices, such as an endoscope, trocar, or other in-vivo imaging device. Optical system 10 may include, for example, illumination source(s) 42, imager 46, and one or more lenses 49 disposed and possibly recessed behind a window 54, for viewing, for example, a target or object 15. One, two, or more than two (for example three, four, six or eight) illumination sources may be used. The one or more lenses 49 may be positioned, for example, along longitudinal axis A of the in-vivo imaging device 40.

In some embodiments of the present invention, imager 46 a lens holder 48 and/or lens 49 may be positioned at any location within the optical system 10, for example according to a manufacturer's instructions or a user such as a physician requirements, and employing different imaging devices with different optical design without the hindrance of backscatter interference.

The course of light rays emitted from illumination source(s) 42 will be followed as an example of the behavior of illumination rays in the optical system 10 according to some embodiment of the present invention. Light 256 may be emitted from an illumination source 42 for illuminating target 15. A percent of the light (represented by ray 217) may be internally reflected from the window 54 internal surface 54' and may be propagated to, for example, the lens 49. A percent of the light 256 (represented by ray 258) may be incident on target 15 (e.g., an object or area in-vivo) and may be reflected or scattered from target 15 and received through aperture 48' and/or lens 49 by imager 46.

According to some embodiments of the present invention it is possible to avoid the backscatter created from light reflecting, for example from the window 54 internal surface 54' to the imager and lenses (represented by ray 217) by positioning blockers in different areas, such as, for example, on a lens holder, in the vicinity of the aperture 48'. For example, a blocker, such as a backscatter blocker 210, may be positioned, for example, above lens 49 so that it will block light rays, such as 217 that are expected to be incident on point 270 on window 54, from which point it is calculated that rays will be internally reflected and will reach the lens 49. That is, point 270 forms a geometrical point of reflection for a light ray incident on point 270 from illumination source 42 and reflected to the imager 46 (via aperture 48' and lens 49), in the absence of backscatter blocker 210. Since the illumination source(s) 42 may be extended illuminations source(s), that is, non pin point illumination source(s), the point of reflection 270 may be an area, or region, of reflection. In general, the term "area of reflection" will be understood to include the limiting case of "point of reflection". The longitudinal axis A may be perpendicular to a backscatter blocker 210.

In actuality, the window 54 is a three dimensional structure. A schematic three dimensional representation of the optical system 10 of FIG. 2A, according to one embodiment, is shown in FIG. 2B.

Figure 2B:
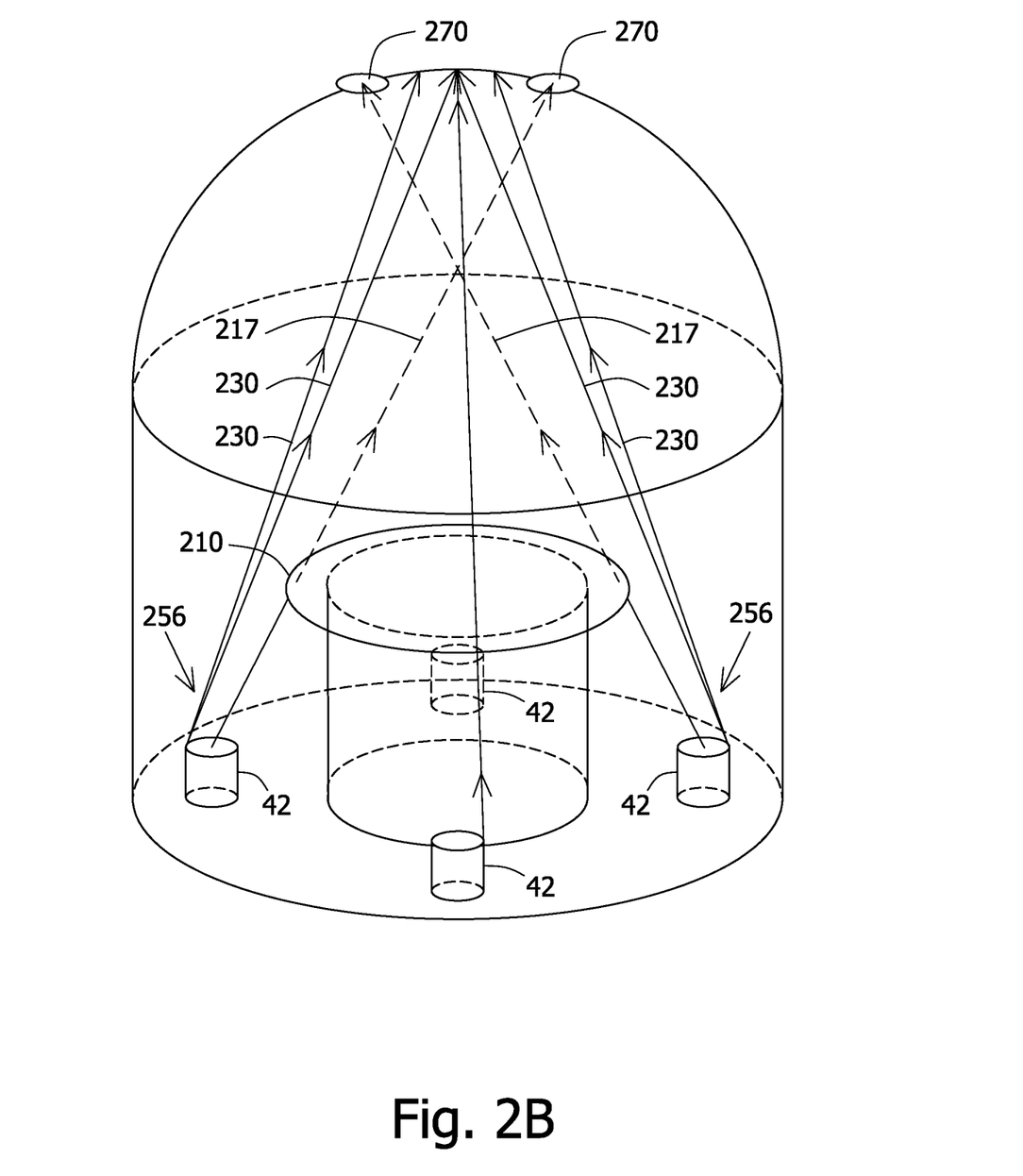

As shown in FIG. 2B the blocking and cutting off a percentage (e.g. rays 217) of the light 256 emitted from illumination source(s) 42 will reduce the light quantity in the vicinity of the window, such as in area 270, but will still cause no dark or shadowed areas on the final image, because only a small percent of the light is being blocked from reaching point 270 and this lack of light is compensated by the other illumination sources. In addition, because the illumination source(s) 42 may be extended illuminations source(s), that is non pin point illumination source(s), the dark and shadowed areas may be compensated by other light rays (e.g. light rays which are not blocked by the backscatter blocker 210) emitting from the illumination source(s) 42.

Figure 3:
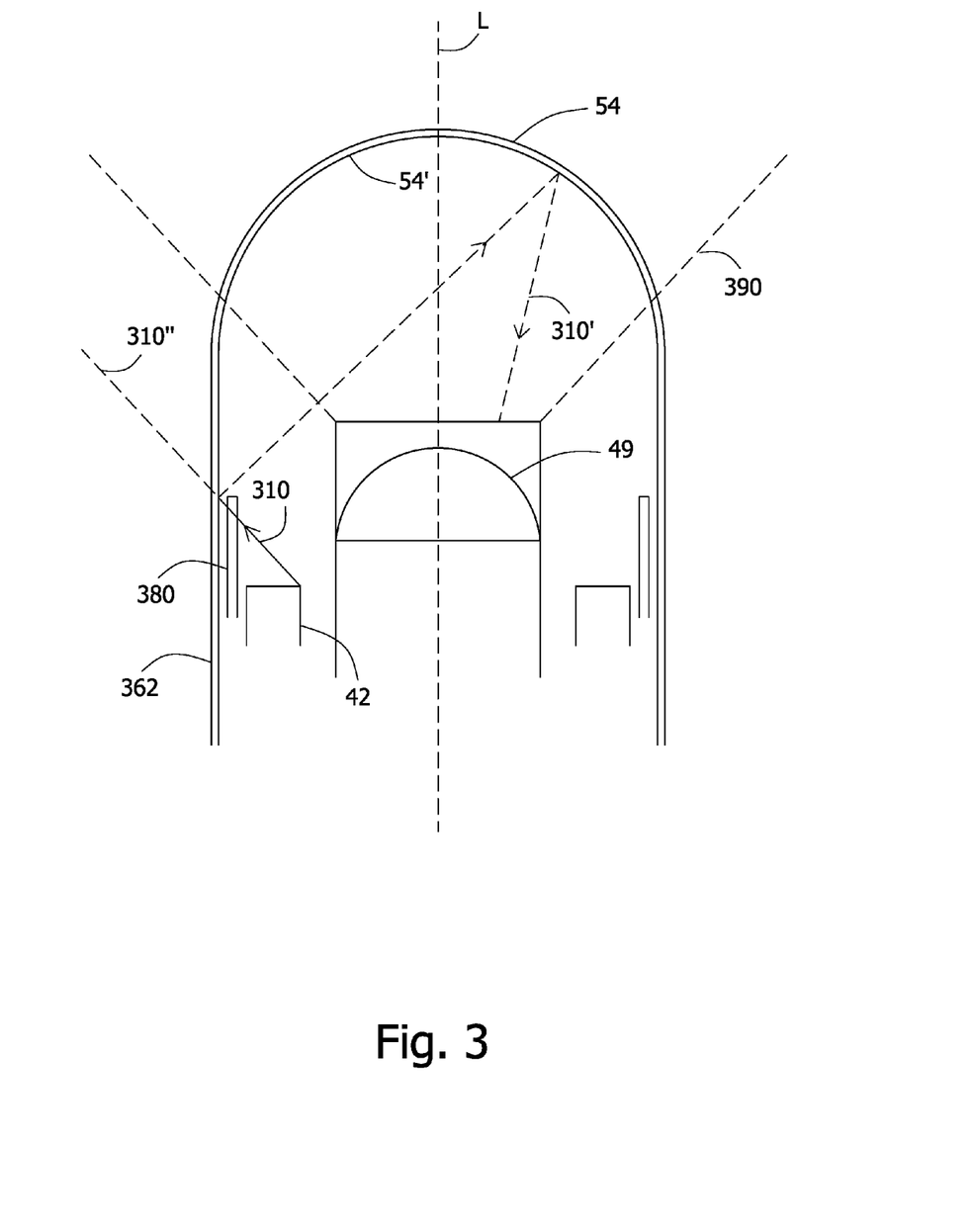
FIG. 3 is a schematic illustration of an optical system according to another embodiment of the present invention.

Reference is now made to FIG. 3 showing a case in which a percent of the light (represented by ray 310) emitted from an illumination source 42 may be internally reflected from a housing 362 of device 40 to the window 54 internal surface 54' and may be propagated to, for example, the lens 49 (represented by ray 310'), thus causing a back-reflection effect. In order to prevent such back-reflection a backscatter blocker, like 380, may be placed in close proximity to the illumination source 42 and block light, such as presented by light ray 310, from reaching specific areas of the window 54. The backscatter blocker 380 may also be placed in close proximity to the housing 362 of device 40. Rays 310 and 310' illustrate an example of light that would reach the lens 49 after two reflections (double reflection backscatter), if the backscatter blocker 380 were absent. As can be seen, double reflection backscatter can be eliminated by positioning the backscatter blocker 380 between the illumination source 42 and a first point of reflection from the internal surface 54'.

Blocking reflecting light rays, such as light ray 310', from reaching specific areas in an in-vivo imaging device such as the optical dome 54 or housing 362 of device 40, will not typically have a visible affect on the quantity or quality of light in the field of view (FOV) of an in-vivo imaging device such as the FOV 390 of device 40. This is due to the fact that a reflected light rays, such as light ray 310 have an obtuse angle in relation to a longitudinal axis L, thus, when not blocked they typically illuminate an area which is usually outside the FOV 390 of an in-vivo imaging device. For example, as shown in FIG. 3, light ray 310" when not blocked by backscatter blocker 380, would have continued to illuminate an area outside FOV 390. The longitudinal axis L may be substantially parallel to the backscatter blocker 380.

Figure 4A:
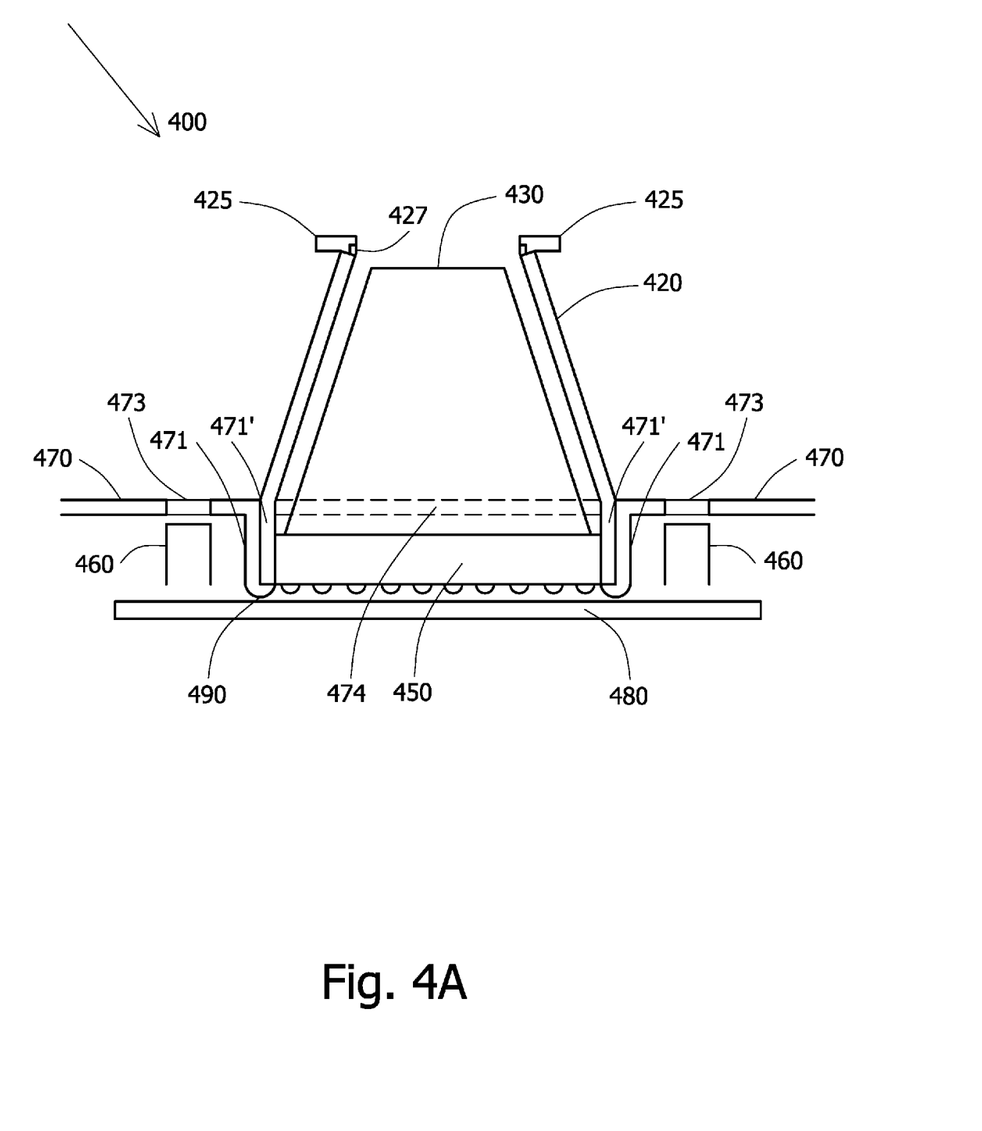
FIG. 4A is a schematic illustration of an optical system including an upper and lower backscatter blocker according to one embodiment of the present invention.

Reference is now made to FIG. 4A showing an assembly 400 for positioning a backscatter blocker on and/or with respect to a lens holder and an illumination source, according to an embodiment of the present invention. When used herein, terms like over, above, on, below, etc., are considered relative terms descriptive when a device is in a certain orientation relative to the viewer; it should be understood that these terms are relative, and given a certain orientation, an optical system may be "below" or "to the side of" an image sensor. According to one embodiment, lens holder 420 together with lens structure 430 may be positioned over imager 450. According to some embodiments, a first backscatter blocker such as an upper backscatter blocker 425 may be placed on lens holder 420 and may be distal to the imager 450, while a second backscatter blocker such as a lower backscatter blocker 470 may be positioned in the vicinity of illumination source(s) 460 and may be proximal to the imager 450. The lens holder 420 and the backscatter blocker 470 may be fixed and or secured with, for example, an adhesive 490 onto a substrate, such as a circuit board 480, with for example, one or more protrusions or legs 471 and 471' of backscatter blocker 470 and lens holder 420. Other fixing and securing methods, for example ultrasonic welding, may be used. The lens holder 420 may incorporate protrusion 427 for assembling the upper backscatter blocker 425 onto and/or over lens holder 420. In some embodiments protrusion(s) 427 may be adhered to the upper backscatter blocker 425 by, for example, gluing, friction fitting, press fitting, welding, laser welding, and/or other suitable methods. Other suitable surfaces, other than and/or in addition to protrusion 427 of lens holder 420 may be used to attach the upper backscatter blocker 425 to lens holder 420. According to one embodiment the upper backscatter blocker may be an integral part of lens holder 420. In one embodiment of the present invention, an indentation or other cavity, etc. may be added to lens holder 420 and/or to the upper backscatter blocker 425 and the lower backscatter blocker, for example so that the upper backscatter blocker 425 and the lower backscatter blocker 470 may, for example, snap into place.

The lower backscatter blocker with openings 473 may be manufactured and or fabricated, with a high degree of accuracy, as may be required, using well-known methods in the art, for example, etching and laser-cutting. Other suitable manufacturing processes may be used as well.

Figure 4B:
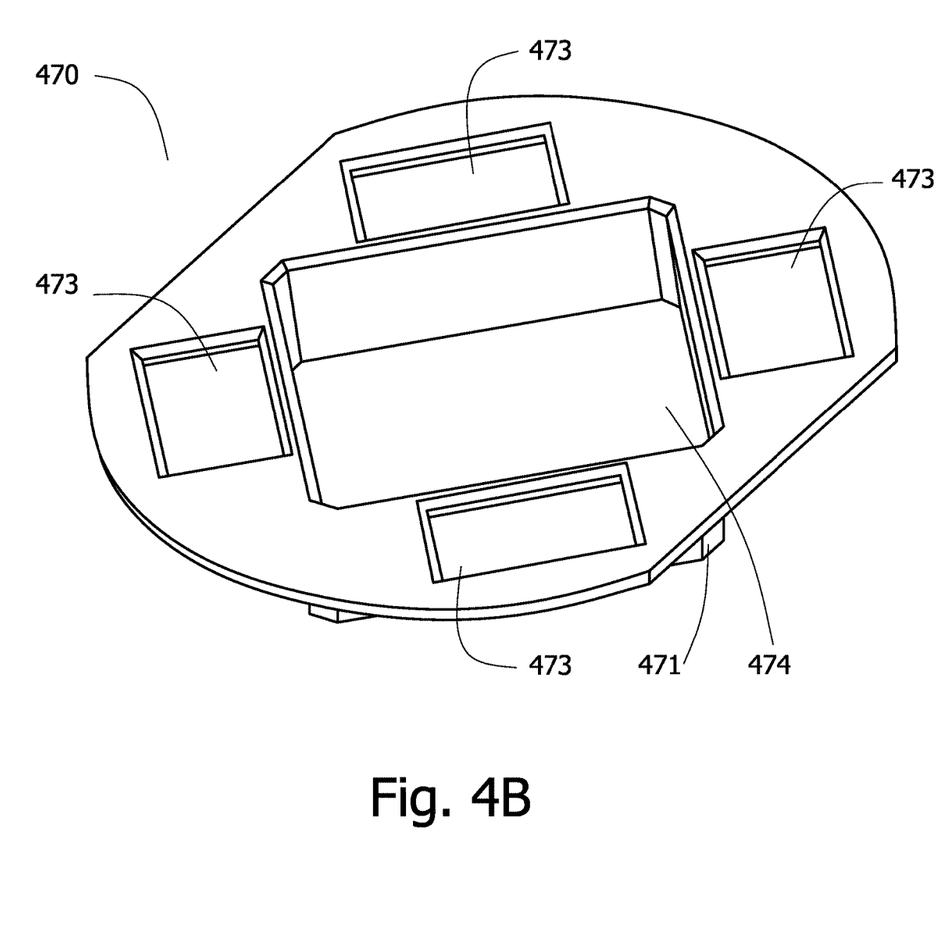
FIG. 4B is a schematic illustration of a backscatter blocker according to one embodiment of the present invention.

Reference is now made to FIG. 4B showing an isometric view of backscatter blocker 470, according to embodiments of the present invention. According to some embodiments of the present invention as shown in FIGS. 4A and 4B, the lower backscatter blocker may include one or more openings, for example four openings 473 for accommodating the illumination source and another opening, such as a square shaped opening 474 for placing the lens holder in the center of the backscatter blocker 470.

According to some embodiments of the present invention, the backscatter blocker 470 may be made from any suitable plastic, e.g. ABS, and manufactured by, for example injection molding or other suitable methods. In some embodiments of the present invention, backscatter blocker 470 may be non-transparent so that light may not penetrate through the backscatter blocker 470. Other suitable materials or methods may be used to manufacture backscatter blocker 470.

Figure 4C:
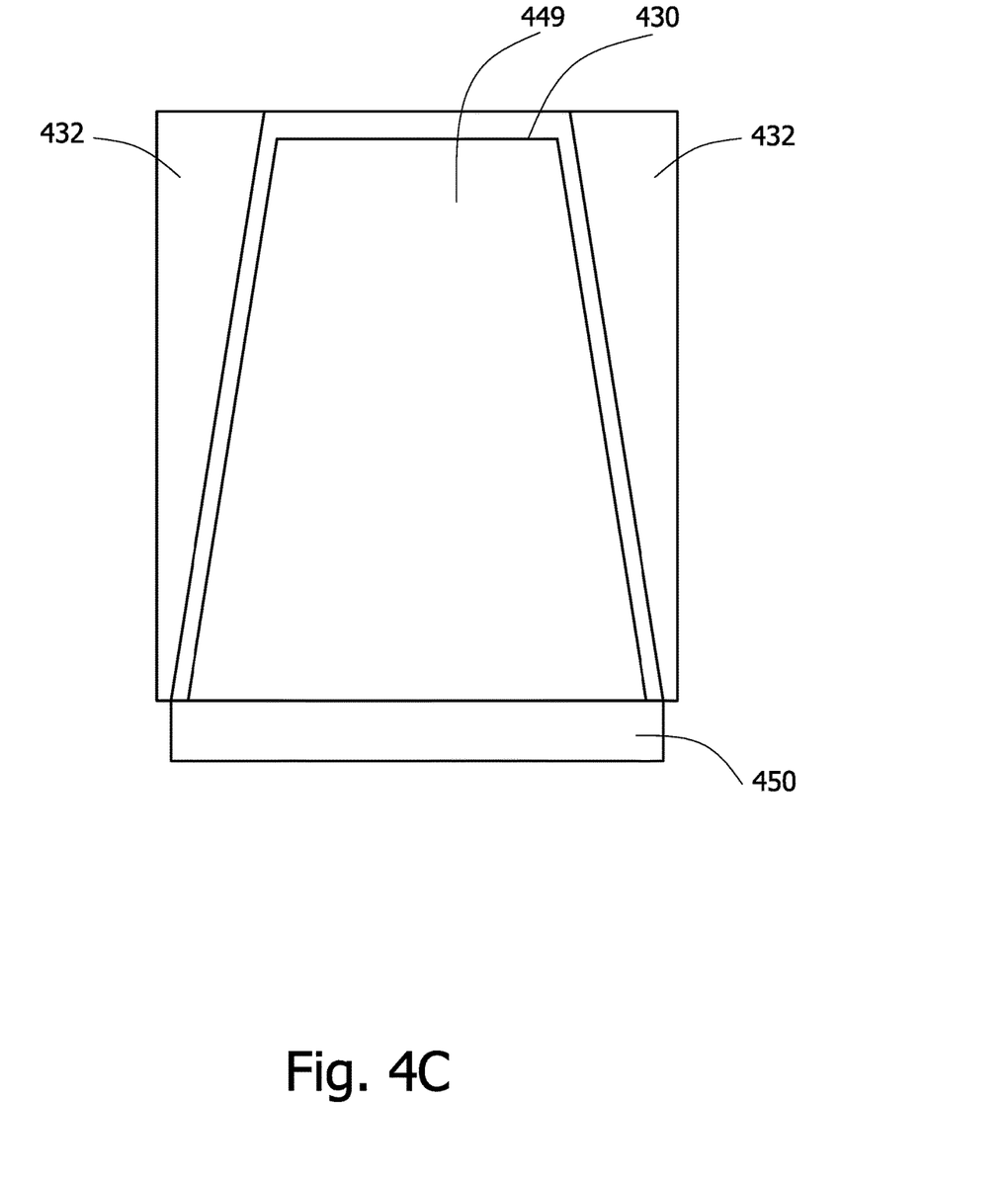
FIG. 4C is a schematic illustration of a lens holder according to one embodiment of the present invention.

Reference is now made to FIG. 4C showing a lens holder 430 positioned, for example over an imager 450 according to embodiments of the present invention. In one embodiment of the present invention, the lens holder 430 may incorporate a backscatter blocker 432 so that the backscatter blocker 432 and the lens holder 430 form a single integral unit. The lens holder which may include a backscatter blocker 432 may be fabricated by, for example, by single cavity injection molding. In an alternate embodiment of the present invention, the lens holder may be manufactured by multi-cavity injection molding where, as a first step for example, an opaque material such as any of the materials mentioned herein which may include a suitable color, may be injected in a mold in, for example, an area of the surrounding wall of lens holder, and as a second step for example, a transparent material may be injected into for example the area in the mold of the lens holder. In another embodiment of the invention the steps may be of a different order or more steps may be added. As such, according to an embodiment of the invention, backscatter blocker 432 may have an opaque section that isolates the imager and/or lens structure 449 from surrounding stray light and a transparent section that includes, for example, lens structure 449.

Figure 5:
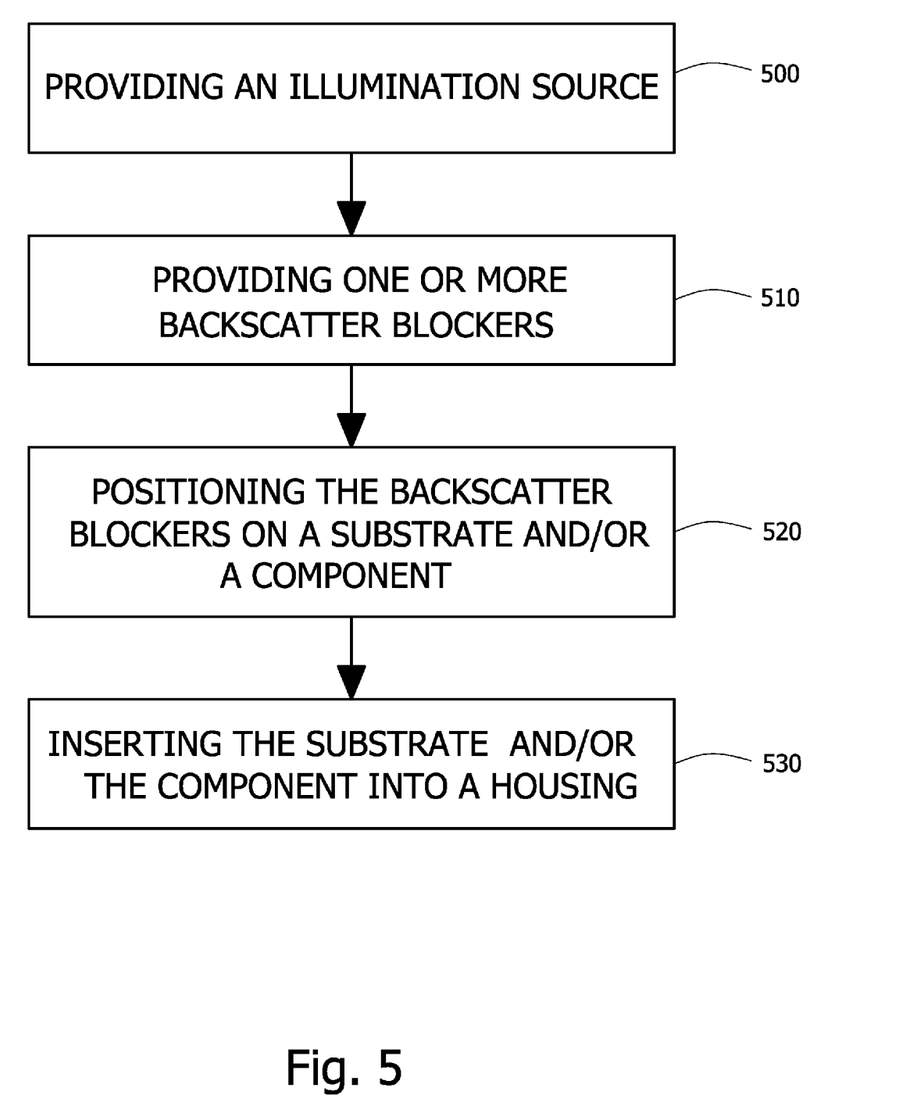
FIG. 5 is a flow chart illustration of a method, according to one embodiment of the present invention.

A method for blocking stray light in an in-vivo imaging device according to some embodiment of the present invention is shown in FIG. 5. According to one embodiment the method may include providing an illumination source (500), providing one or more backscatter blockers (510) and positioning the backscatter blockers on a substrate and/or a component (520) of the imaging device, for example on a Printed Circuit Board (PCB) and/or a lens holder or an illumination source, so that the backscatter blockers will prevent rays from reaching an area on the viewing window from which light will be internally reflected onto the imager, causing undesired glare. According to some embodiments the method may further include inserting the substrate and/or the component into a housing of an in-vivo device (530). According to some embodiments the area on the viewing window from which light will be internally reflected is calculated by using computer programs, like LightTools or TracePro, that simulate a three dimensional optical unit and a realistically distributed in space and angles light source. According to some embodiments calculations may be performed using the non-sequential method of Zemax, Code-V or OSLO programs.

It will be appreciated by persons skilled in the art that the present invention is not limited to what has been particularly shown and described hereinabove. Rather the scope of the present invention is defined only by the claims which follow.

The invention claimed is:

1. An in vivo imaging device having a central longitudinal axis, the in vivo imaging device comprising:
    a dome shaped viewing window;
    an illumination source;
    an imager; and
    at least one barrier positioned to block light from the illumination source from reaching at least one specific spot on the dome shaped viewing window, the at least one barrier placed at a position along a radius of a section of the device perpendicular to the central longitudinal axis of the device that is between the illumination source and said dome shaped viewing window, wherein the imager, the at least one illumination source and the at least one barrier are situated on the concave side of the dome shaped viewing window.

2. The in vivo imaging device according to claim 1, wherein the at least one barrier is in close proximity to said illumination source.

3. The in vivo imaging device of claim 1 comprising a plurality of illumination sources.

4. The in vivo imaging device of claim 1 wherein the at least one barrier is positioned along the radius closer to the window than to the central longitudinal axis.

5. The in vivo imaging device of claim 1 wherein the at least one barrier extends along the direction of the central longitudinal axis to a plane perpendicular to the longitudinal axis closer to the apex of the dome than is the illumination source.

6. The in vivo imaging device of claim 1 wherein the device is a swallowable capsule.

7. The in vivo imaging device of claim 1 comprising a transmitter, wherein the imager is configured to send data representing images captured to the transmitter for transmitting said data.

8. The in vivo imaging device of claim 1 wherein the at least one barrier is positioned along the radius at a position that is not between the illumination source and the imager.

9. The in vivo imaging device of claim 1, wherein the at least one barrier is positioned on a plane parallel to a plane of the imager.

10. An in vivo imaging device having a central longitudinal axis, the in vivo imaging device comprising:
    a dome shaped viewing window;
    an illumination source;
    an imager; and
    a barrier positioned to block light emitted from said illumination source from reaching at least one specific spot on the imager, the barrier positioned along a radius of a section of the device perpendicular to the central longitudinal axis of the device that is between the illumination source and the dome shaped viewing window and not between the illumination source and the imager;
    wherein the imager, the illumination source and the barrier are situated on the concave side of said dome shaped viewing window.

11. The in vivo imaging device according to claim 10, wherein the barrier is in close proximity to said illumination source.

12. The in vivo imaging device of claim 10 comprising a plurality of illumination sources.

13. The in vivo imaging device of claim 10 wherein the barrier is positioned along the radius closer to the window than to the central longitudinal axis.

14. The in vivo imaging device of claim 10 wherein the barrier extends along the direction of the central longitudinal axis to a plane perpendicular to the longitudinal axis closer to the apex of the dome than is the illumination source.

15. The in vivo imaging device of claim 10 wherein the device is a swallowable capsule.

16. The in vivo imaging device of claim 10 comprising a transmitter, wherein the imager is configured to send data representing images captured to the transmitter for transmitting said data.

17. The in vivo imaging device of claim 10, wherein the barrier is positioned on a plane parallel to a plane of the imager.

* * * * *